US009593381B2

(12) United States Patent
Kirveskari et al.

(10) Patent No.: US 9,593,381 B2
(45) Date of Patent: Mar. 14, 2017

(54) METHOD AND KIT FOR DETECTING CARBAPENEMASE GENES

(75) Inventors: Juha Kirveskari, Helsinki (FI); Suvi Koskela, Helsinka (FI)

(73) Assignee: Amplidiag OY, Helsinki (FI)

( * ) Notice: Subject to any disclaimer, the term of this patent is extended or adjusted under 35 U.S.C. 154(b) by 1069 days.

(21) Appl. No.: 13/297,020

(22) Filed: Nov. 15, 2011

(65) Prior Publication Data

US 2012/0129180 A1 May 24, 2012

Related U.S. Application Data

(63) Continuation-in-part of application No. PCT/FI2010/050395, filed on May 17, 2010.

(30) Foreign Application Priority Data

May 15, 2009 (FI) ...................................... 20095544

(51) Int. Cl.
*C12P 19/34* (2006.01)
*C12Q 1/68* (2006.01)

(52) U.S. Cl.
CPC ......... *C12Q 1/689* (2013.01); *C12Q 2600/16* (2013.01)

(58) Field of Classification Search
USPC .............................. 435/6.12, 91.2; 536/24.33
See application file for complete search history.

(56) References Cited

U.S. PATENT DOCUMENTS

| 7,045,291 | B2 * | 5/2006 | Hanson et al. | ............... | 435/6.13 |
| 7,968,292 | B2 * | 6/2011 | Whiteford et al. | ........... | 435/6.12 |
| 2005/0202460 | A1 * | 9/2005 | Leighton et al. | .................. | 435/6 |
| 2009/0317807 | A1 * | 12/2009 | Hanson | ............................. | 435/6 |

FOREIGN PATENT DOCUMENTS

| JP | 2006115811 | 5/2005 |
| JP | 2007195421 | 8/2007 |
| KR | 20080029726 | 4/2008 |
| WO | 02/082086 | 10/2002 |
| WO | 03/048377 | 6/2003 |
| WO | WO 2007/140004 A2 | 12/2007 |

OTHER PUBLICATIONS

PCT/FI2010/050395 PCT International Preliminary Report on Patentability; Apr. 7, 2011.
PCT/FI2010/050395 Written Opinion of the International Searching Authority; Aug. 16, 2010.
Queenan, Anne Marie, et al; Carbapenemases: the versatile beta-lactamases; Clinical Microbiology Reviews, Washington D.C.; Jul. 1, 2007; vol. 20, No. 3, pp. 440-458.
Zhuo, C., etal; Pseudomonas aeruginosa isolate 10020 metallo-beta-lactamase IMP-9 (blaIMP-9) gene, patrial cds.
Poirel, L, et al; Klebsiella pneumoniae strain 11978 insertion sequence IS1999, complete sequence.
Japanese Office Action issued for Japanese Patent Application No. 2012-510325, mailed on Sep. 19, 2014.
Lee, et al. Characterization of blaCMY-11, an AmpC-type plasmid-mediated B-lactamase gene in a Korean clinical isolate of *Escherichia coli*, J. Antimicrob. Chemother. (2002) 49, 269-273.
Yong, et al. "Characterization of a New Metallo-B-Lactamase Gene, BlaNDM-1, and a Novel Erthromycin Esterase Gene Carried on a Unique Genetic Structure in Klebsiella pneumoniae Sequence Type 14 from India," Antimicrobial Agents and Chemotherapy, vol. 53. No. 12, p. 5046-5054 (Dec. 2009).
Ellington, M. J. et al., "Multiplex PCR for rapid detection of genes encoding acquired metallo-beta-lactamases", The Journal of Antimicrobian Chemotherapy, 2007, vol. 59, pp. 321-322.
Australian Patent Office Examination Report dated Jul. 10, 2015.
Bradford, P.A. et al. Emergence of cabapenem-resistant Klebsiella species possessing the class A carbapenem-hydrolyzing KPC-2 and inhibitor-resistant TEM-30 beta-lactamases in New Youk Clti. Clinical Infectious Diseases 2004, vol. 39: pp. 55-50.
Japan Patent Office Office Action dated on Sep. 1 2015.

* cited by examiner

*Primary Examiner* — Kenneth Horlick
(74) *Attorney, Agent, or Firm* — Berggren, Inc.

(57) ABSTRACT

The present invention relates to a method and kit for detecting carbapenemase resistance genes causing carbapenem resistance in bacteria. The invention provides oligonucleotide primers, which can be used in the detection. The method can be used to detect OXA-48, SME, GIM-1, VIM 1-22, SPM, GES 1-10, KPC 1-7, IMI 1-3/NMC-A, IMP 1-24 within a single reaction and OXA-23 group, OXA-24 group, OXA-51 group with ISabal promoter, OXA-55, OXA-58, OXA-60, OXA-62, CMY 1, -10, -11 SFC-1, NDM-1, and SIM-1 within another single reaction.

8 Claims, 4 Drawing Sheets

METHOD AND KIT FOR DETECTING CARBAPENEMASE GENES

PRIORITY CLAIM

This is a continuation-in-part application of International application number PCT/FI2010/050395 filed on May 17, 2010 claiming priority of the Finnish national patent application number 20095544 filed on May 15, 2009, the contents fo both of which are incorporated herein by reference in their entirety.

SEQUENCE LISTING

This application contains sequence data provided in computer readable form and as PDF-format. The PDF-version of the sequence data is identical to the computer readable format.

FIELD OF THE INVENTION

The present invention relates to a method and kit for detecting carbapenemase genes causing carbapenem resistance in bacteria (i.e. carbapenem resistant bacteria). The invention relates also to oligonucleotide primers which can be used in the detection.

BACKGROUND OF THE INVENTION

The increase of resistance against β-lactam antibiotics, such as penicillins and kefalosporins, present treatment problems of infections caused by Gram negative rods. Therefore, more and more often β-lactam antibiotics must be replaced with broad-spectrum antibiotics.

Carbapenems represent an important broad-spectrum antibiotic group for treating difficult hospital infections. Carbapenems are typically effective against most aerobic Gram positive and Gram negative bacteria and also against anaerobes. Often used carbapenems are imipenem, meropenem and ertapenem. Bacterial strains resistant against these pharmaceuticals appear in hospital patients particularly in Greece, Israel, United States, Turkey and Far East (China) and in Central America.

Typical bacteria with reduced carbapenem susceptibility are *E. coli, Klebsiella* sp. and other Enterobacteriaceae sp. In addition, *Pseudomonas aeruginosa*, and its closely related species from environmental origin, and *Acinetobacterium* sp. occurring in patients with compromised immune response, often have reduced carbapenem susceptibility. More specifically clinically relevant pathogens may be *E. coli; Klebsiella pneumoniae, Pseudomonas aeruginosa* and *Acinetobacter baumannii*, and there is often no proper antibiotic treatment available due to multi resistant overall phenotype of these super bacteria. Traditional biochemical methods are slow and unspecific and thus early detection of these strains requires new molecular methods.

The reduced susceptibility to carbapenem actibiotics may be caused by one or more of hundreds different β-lactam antibiotic resistance genes combined with changes in cell wall permeability (e.g. specific porine changes) and/or active efflux-associated with hyperproduction of ampC β-lactamases. Typically this causes reduction of carbapenem susceptibility, which is often reversible, and ends when the antibiotic treatment is finished. The reason for this is that the maintenance of the mechanism is energy consuming to the bacterium and disadvantage for its nutrient supply.

Another and more serious reason for carbapenem resistance is enzymes degrading carbapenem antibiotics, so called carbapenemases. In the presence of carbapenemases the bacterium does not need to offer significantly its capability for competition compared with wild type bacteria. Therefore, carbapenemases may alone be the reason for remarkable carbapenem resistance. This mechanism may appear combined to the earlier mentioned mechanisms, which increases the reduction of the susceptibility and consequently the resistance. Carbapenemase genes may be present both in chromosomes and in plasmids. In particular those located in plasmids, are easily transferred to other bacterial species, similarly as those in extended spectrum β-lactamase (ESBL) strains. Strains producing carbapenemase are often also ESBL-strains. Especially, *Klebsiella pneumoniae* carbapenemases (KPC)- and Verona imipenemase (VIM)-gene family are a potential threat to currently available antibiotic treatments. Since KPC-producing bacteria may be difficult to detect, based on routine antibiotic susceptibility testing, they may cause problems in infection control measures. Another common β-lactamase family with carbapenemase properties is Guiana extended spectrum β-lactamase (GES) which is also particularly difficult to detect based on routine antibiotic susceptibility testing.

Large reservoir of carbapenem resistance genes in environmental species combined with increasing carbapenem use provoke the risk of emergence of rare or new carbapenemase genes, which may remain undetected. On the other hand carbapenem resistance may be caused by reversible mechanism as described above. Therefore, there is a need for improved methods for detecting carbapenemase genes causing carbapenem resistant bacteria in biological samples. Traditional biochemical methods are slow and unspesific and thus early detection of these strains requires new molecular methods.

SUMMARY

It is an aim of the present invention to solve at least some of the problems of the prior art.

In particular, it is an aim of the invention to provide a method for finding out whether a biological sample contains bacteria resistant to carbapenem antibiotic group. More specifically, it is an aim of the invention to provide a method for screening carbapenemase genes causing carbapenem resistance in bacteria i.e. causing resistance to carbapenem group antibiotics.

The present invention is based on the use of molecular biology methods to screen resistance genes from biological samples. In particular, the invention is based on the use of specifically designed primers capable of detecting carbapenemase genes causing carbapenem resistance. These methods can be used to replace biochemical methods or combined with these.

The present invention provides a method for detecting carbapenemase genes causing carbapenem resistance in bacteria (carbapenem resistant bacteria) present in a biological sample.

The invention provides also a kit and primers for identifying carbapenemase genes. Furthermore, the invention provides an arrangement for identifying carbapenemase genes. The invention has many advantages. It makes possible to identify quickly strains which threaten the hygiene of hospitals and continuous follow-up. This is only partly possible by using biochemical methods. The use of molecular biology methods alone or in combination with biochemical methods is a remarkable improvement over the prior art.

The method and kit according to this invention provides new solutions to detect carbapennemase genes, such as Real-Time polymerase chain reaction. Due to multiple underlying genomic mechanisms, the instant invention provides a highly multiplex assay to detect at least the most important, horizontally spreading genes.

In the following the invention will be examined more closely with the aid of a detailed description and with reference to some working examples.

SHORT DESCRIPTION OF THE DRAWINGS

Figure 1:
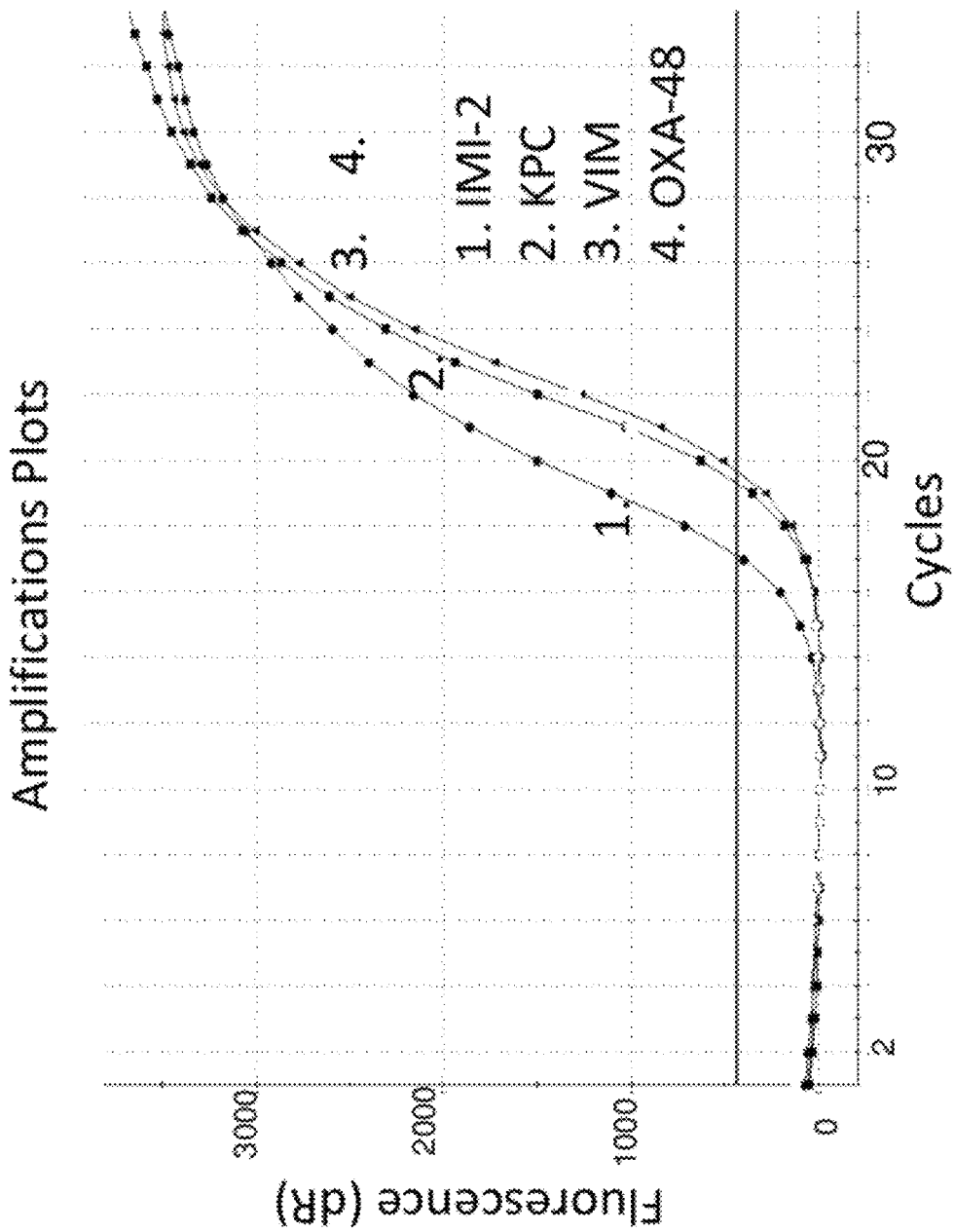
FIG. 1 shows a gene amplification curve of four different carbapenemase genes.
Figure 2:
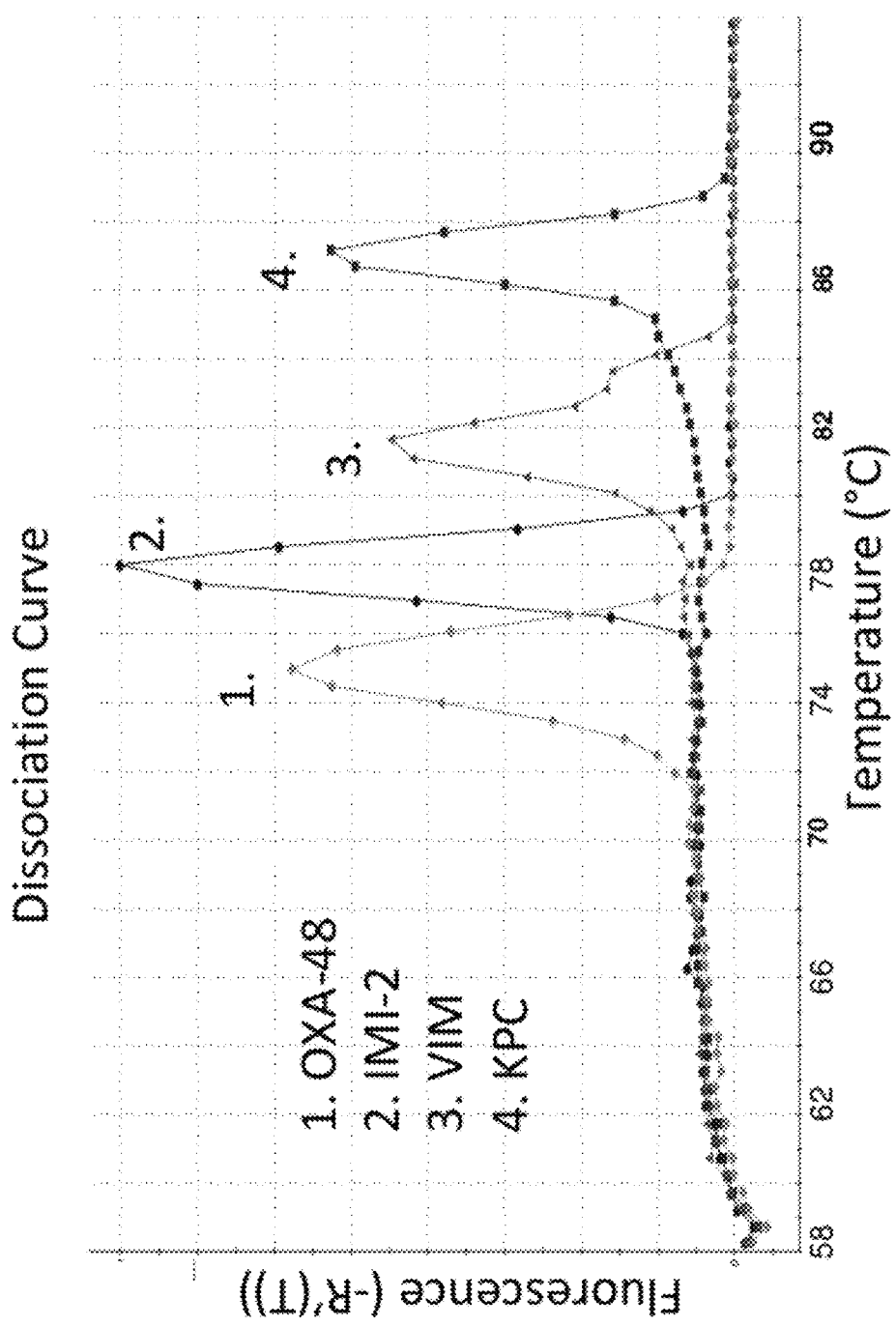
FIG. 2 shows a melting curve analysis, different gene products can be separated on the basis of their different melting temperature.
Figure 3:
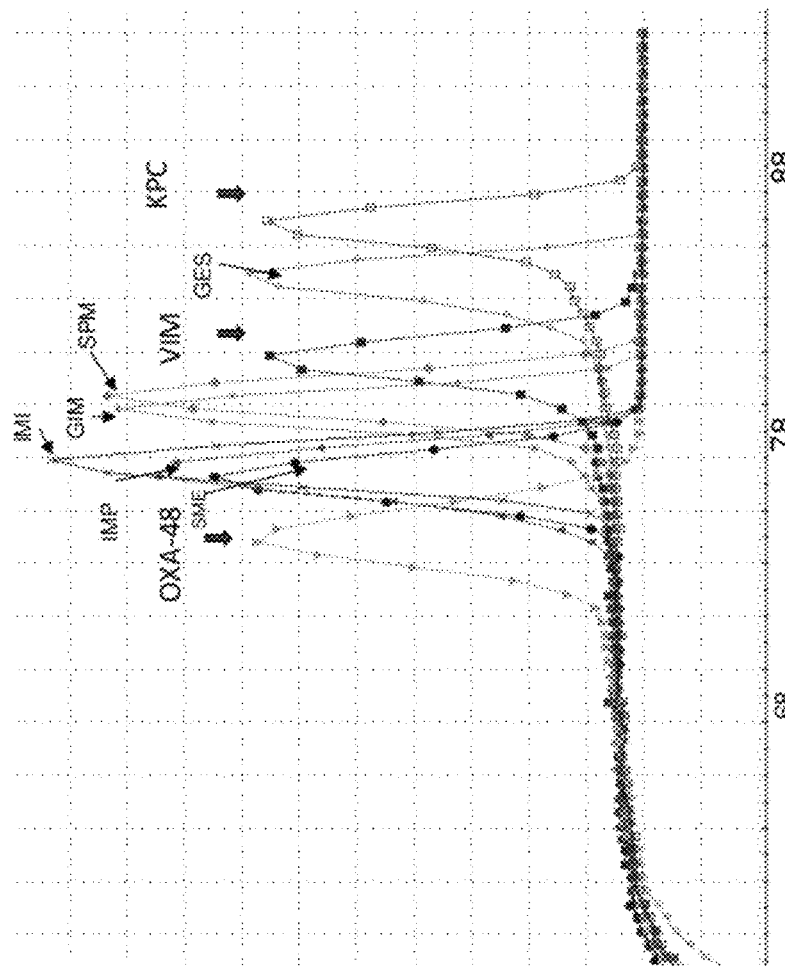

FIG. 3. shows dissociation curve for the first multiplex in the assay described in Example 3. Different gene products can be separated on the basis of their different melting temperatures.

Figure 4:
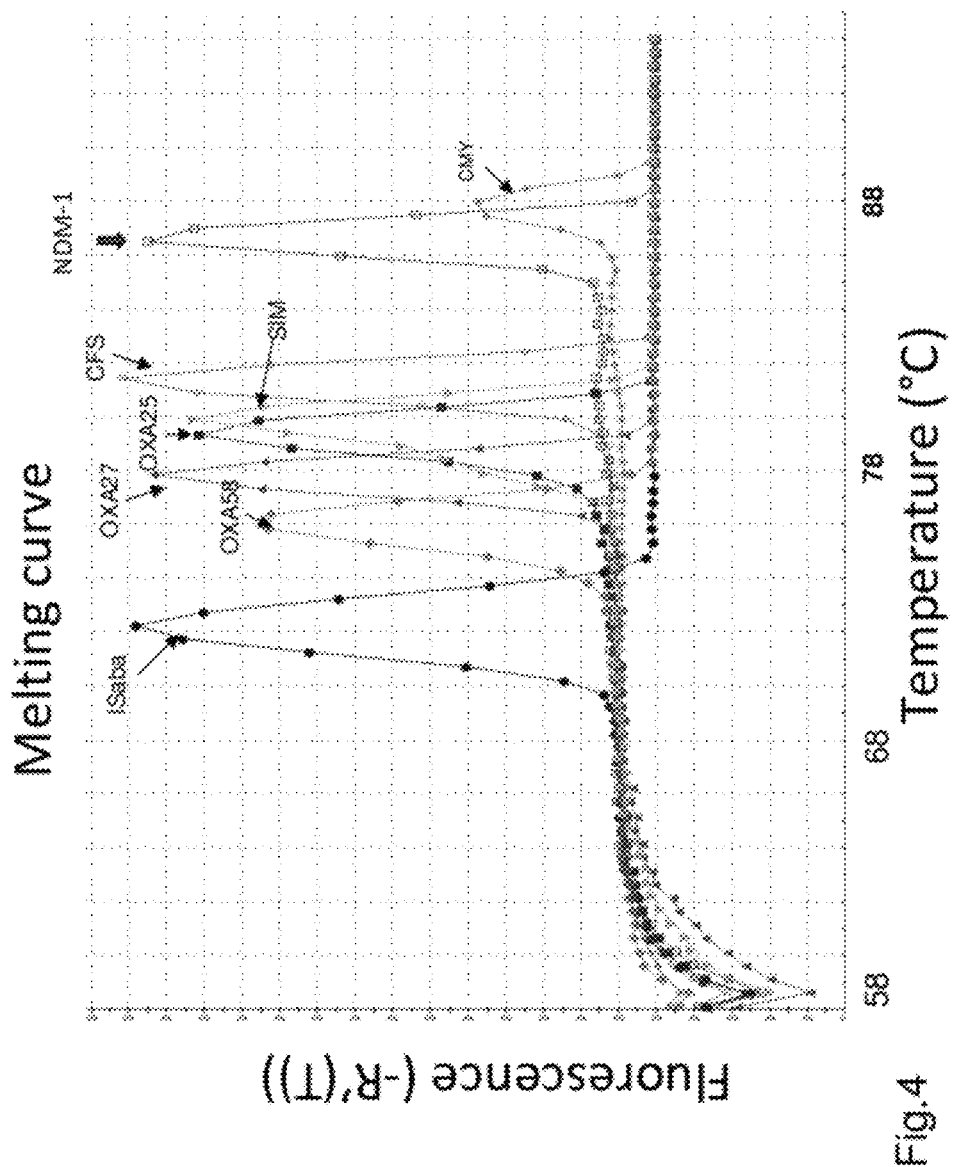

FIG. 4. shows dissociation curve for the second multiplex in the assay described in Example 3. Different gene products can be separated on the basis of their different melting temperatures.

DETAILED DESCRIPTION OF THE INVENTION

The present invention makes it possible to screen for genes resistant to carbapenem antibiotics. The method is based on the detection of carbapenemase genes causing carbapenem resistance in bacteria. More specifically the screening is based on the use of an amplification method, such as LCR (Ligase Chain Reaction) or PCR (Polymerase Chain Reaction) method.

Preferably the amplification reaction is a PCR method, in particular real time PCR. More advantageously, the method uses PCR based on real time SYBR Green detection and preferably melting curve analysis of the product.

By SYBR Green is here meant a nucleic-acid-binding fluorescent dye illuminating amplified product with nucleic-acid-binding fluorescent dye bound thereto with a selected wavelength of light for eliciting fluorescence therefrom and monitoring fluorescence emission and determining a cycle when the fluorescence emission reaches a plateau phase, indicating the completion of the reaction. Preferably, the nucleic-acid-binding fluorescent dye is a member selected from the group consisting of SYBR™ GREEN I, ethidium bromide, pico green, EVA Green, acridine orange, thiazole or ange, YO-PRO-1, and chromomycin A3.

By real time SYBR Green detection is here meant a method of real time monitoring of a polymerase chain reaction amplification of a target nucleic acid sequence in a biological sample. The method comprises amplifying the target sequence by polymerase chain reaction preferably in the presence of SYBR™ Green I, the polymerase chain reaction comprising the steps of adding a thermostable polymerase and primers for the targeted nucleic acid sequence to the biological sample and thermally cycling the biological sample between at least a denaturation temperature and an elongation temperature; exciting the biological sample with light at a wavelength absorbed by the SYBR™ Green I and detecting the emission from the biological sample; and monitoring the temperature dependent fluorescence from the SYBR™ Green I. Preferably, the monitoring step comprises determining a melting profile of the amplified target sequence.

By "biological sample" is here meant a direct clinical sample, for example bodily fluids such as blood or urine, or throat swabs, nasal swabs, dermal swabs, sputum, feces or bronchial aspirates. The biological sample may also mean pure cultures of bacteria from various environments. Typically the bacterial cultures may be prepared from biological samples by plating and growing the bacteria.

An amplification reaction, typically a PCR reaction, can be used to amplify the nucleic acids directly in a biological sample, which is here typically a clinical sample, or in a pure culture of bacteria, or the amplication reaction, typically a PCR reaction, can be used to amplify isolated nucleic acids.

By "primers" are here meant oligonucleotides designed to be specific for polynucleotides to be detected. Primers can be designed to comprise or have a sequence complementary to the target polynucleotide sequence. Forward and reverse primers can be designed which are capable of hybridizing through base pairing to the target polynucleotide. In one embodiment of this invention primers are designed to detect carbapenemase genes expected to cause carpabenem resistance. In a preferred embodiment of the invention the primers contain at least part or comprise or have the sequences selected from the group comprising SEQ ID NO: 1 to SEQ ID NO: 49.

The primers are preferably 15 to 50 nucleotides long, typically 20 to 40, or 20 to 35 nucleotides long. Additional nucleotides, for example 1, 2 or 3, may be added to either or both ends of the primers. Alternatively 1, 2 or 3 nucleotides may be deleted from or substituted in either or both ends of the primers. In some cases 1, 2 or 3 nucleotides may be added, deleted or substituted in the middle i.e. in other parts than the terminal parts of the primer.

Modifications (in particular genetical modifications) or partial sequences of primers are possible as long as the primer has enough complementarity with the target nucleic acid sequence being capable of hybridizing to the target nucleic acid sequence. Within the scope of the present invention are modified primers or partial sequences of primers being still capable of detecting the target polynucleotide sequences, i.e. the genes responsible of carbapenem resistance, carabapenemase genes.

The hybridization conditions are preferably stringent conditions and refer here to hybridization at 58° C.+/−7° C., preferably +/−3° C. The test can be run on using commercial PCR master containing optimal concentration of ions, e.g. Mg2+, K+ and NH4+ for primer hybridization (annealing if PCR) and extension reactions. For example, MAXIMA SYBR qPCR Master Mix which use low amount of SYBR Green for high PCR efficiency. The components in the reaction are 10 microliters qPCR master mix, 6.8 microliters of oligomix 1, or 6.4 microliters of oligomix 2, and 1 microliter DNA template.

By using biochemical methods only it is not possible to solve the genetic mechanisms behind the carbapenem resistance, because the resistance is caused by more than 110 genes. The knowledge of the resistance mechanism improves essentially the interpretation of antibiotic susceptibility assay and the choice of pharmaceuticals used to treat the patient. For example, carbapenemases with broad substrate spectrum, such as VIM, discourage in vivo use of any β-lactam antibiotic, whereas other mechanisms, such as IMI may leave some β-lactam treatment options available.

The present disclosure provides primers, which have been designed to detect genes responsible of the carbapenem resistance (i.e. carbapenemase genes causing carbapenemase resistance). The primers have been experimentally tested and optimized. According to one preferred embodiment of the invention the identification reaction is carried out in two separate reactions. In these reactions the amplification conditions are commonly compatible. This makes possible HTP screening (high throughput screening).

Consequently, the method makes possible to minimize the testing costs. The method is also simple and user-friendly. Furthermore, the method is suitable for everyday diagnostic use.

According to a preferred embodiment of the invention the test can identify 110 resistance genes with their subvariants. This is carried out preferably in two (or more, preferably two) multiplex PCR reactions based on real time SYBR Green based identification and with determination of the dissociation temperature.

According to one preferred embodiment of the invention one (or the first) multiplex reaction covers more than 99% of carbapenemases within Enterobacteriaceae. By using the first multiplex reaction it is possible to screen coliform rods belonging to Enterobacteriaceae.

According to another preferred embodiment of the invention one other (the second) multiplex reaction is aimed in particular for screening multiresistant bacteria from patients being immunocompromized. Typically these are bacteria belonging to *Pseudomonas* sp. and *Acinetobacterium* sp.

According to one further embodiment one (or the first) multiplex reaction typically detects group B metallo-β-lactamase genes, most of group A carbapenemase genes (penicillinase genes) and OXA-48 gene belonging to group D (oxasillinases). The other (or second) multiplex reaction typically detects group D carbapenemase genes (oxasillinase genes) group C carbapenemase genes (cefalosporinase genes) and SFC gene belonging to group A (penicillinases) and NMD-1.

According to one preferred embodiment of the invention the method comprises the steps:
1 and 2. Preparing the Biological Sample.

This may comprise the isolation of the nucleic acid. This is typically carried out by boiling or semi-automatically by extraction robot. The sample may be used also directly or pure cultures of bacteria prepared from the sample may be used.
3. Gene amplification:
a) master mix comprising polymerase and PCR buffer;
b) nucleoside triphosphate monomers;
c) oligonucleotide primers for the reactions;
d) nucleic acid template from the sample;
e) amplifying and analyzing the dissociation curves of the products. This is preferably carried out by real time PCR equipment.
4. Analyzing the results
a) positive and negative controls present;
b) dissociation temperature indicates often the mechanism; the result can be confirmed by sequencing of the product in a separate reaction, if needed
c) negative result excludes with high probability carbapenemases, since the test comprises essentially all carbapenemase genes disclosed in clinical species. Nucleic acid isolated from the sample and nucleic acid template is preferably DNA. Since the majority of the samples are negative, the screening method is very effective and high throughput in its nature.

In a preferred embodiment of the invention the oligonucleotide primers are designed for the detection of genes or gene families or gene subvariants selected from the group comprising:
VIM 1-22, IMP 1-24, OXA-48, KPC 1-7, GES 1-10, SPM, NMC-A, IMI 1-3, SME 1-3, GIM-1, and SIM-1.

According to a more preferred embodiment, at least one of each of the genes or gene families is detected in one reaction. In still more preferred embodiments more than one gene or gene family or more than one gene subvariant or all the genes or gene families or gene subvariants are detected in one reaction.

In another preferred embodiment of the invention the oligonucleotide primers are designed for the detection of genes or gene families or their subvariants selected from the group comprising:
OXA-24-25, 26, -40, -72, OXA-23, -27, OXA-50, OXA-51, 64-66, 68-71, 75-78, 83, 84, 86-89, -92, -94, -95, OXA-55, OXA-58, OXA-60, OXA-62, SFC-1, and CMY-1, -10.

According to a more preferred embodiment, at least one of each of the genes or gene families is detected in one reaction. In still more preferred embodiments more than one gene or gene family or more than one gene subvariant or all the genes or gene families or gene subvariants are detected in one reaction.

In a further preferred embodiment of the invention at least one of each of the OXA genes or gene families are detected in one reaction, more preferably more than one gene or gene family or more than one subvariant or all the OXA genes or gene families or subvariants are detected in one reaction.

In one further preferred embodiment of the invention the oligonucleotide primers are designed for the detection of genes or gene families or their subvariants selected from the group comprising:
OXA-48, SME, GIM-1, VIM 1-22, SPM, GES 1-10, KPC 1-7, IMI 1-3/NMC-A, IMP 1-24.

According to a more preferred embodiment, at least one of each of the genes or gene families is detected in one reaction. In still more preferred embodiments more than one gene or gene family or more than one gene subvariant or all the genes or gene families or gene subvariants are detected in one reaction.

In one other further preferred embodiment of the invention the oligonucleotide primers are designed for the detection of genes or gene families or their subvariants selected from the group comprising:
OXA-23 group, OXA-24 group, OXA-51 group with ISabal promoter, OXA-55, OXA-58, OXA-60, OXA-62, CMY 1, -10, -11 SFC-1, NDM-1, and SIM-1.

According to a more preferred embodiment, at least one of each of the genes or gene families is detected in one reaction. In still more preferred embodiments more than one gene or gene family or more than one gene subvariant or all the genes or gene families or gene subvariants are detected in one reaction.

NDM-1 is a new metallo-β-lactamase (MBL) from India and Pakistan, which shares very little identity with other MBLs, with the most similar MBLs being VIM-1/VIM-2, with which it has only 32.4% identity. NDM-1 can hydrolyze all β-lactams except aztreonam. Compared to VIM-2, NDM-1 displays tighter binding to most cephalosporins, in particular, cefuroxime, cefotaxime, and cephalothin (cefalotin), and also to the penicillins. NDM-1 may conjugate in vivo to the other bacterial species, which is mediated by transconjugant plasmid.

Although most reliable result of carbapenemase resistance in a biological sample can be obtained by studying the presence of many carbapenemase genes, most important genes (or gene families or gene subvariants) to be detected are selected from the group comprising: KPC 1-7, OXA-48, VIM 1-22, GES 1-10, and/or IMP1-24. Most important to detect is KPC 1-7, second most important are OXA-48 and/or VIM 1-22, third important is GES 1-10, and fourth important are IMP1-24.

Furthermore, important to detect are also genes (or gene families or gene subvariants) SME 1-3, GIM-1, SPM and/or IM11-3/NMC-A.

Also important to detect are genes (or gene families or gene subvariants) OXA-23 group, OXA-24 group, OXA-51 group with ISabal promoter, OXA-58 and/or NDM-1. Furthermore, important to detect are also CMY-1, -10, -11, SFC-1, and/or SIM-1 genes (or gene families or gene subvariants). Also OXA-55, OXA-60 and/or OXA-62 genes (or gene families or gene subvariants) can be detected.

However, which genes are most important to detect depends also on the geographical area i.e. the prevalence of certain resistance genes and/or bacteria on that geographical area.

All the above mentioned genes have been described in the literature. The test has been validated in addition to positive control strains also with more than 250 clinical ESBL strains, with more than 50 multiresistant *Acinetobacter-* and *Pseudomonas* strains and with about 60 other negative control strains (specificity) covering most important clinical aerobic rods.

In developing the oligonucleotide primers capable of being used in the instant assay, the desired oligonucleotide sequences were chosen based on:

i) maximal theoretical coverage of different functional gene variants by sequence alignment of the genes, and ii) on balanced amplification, e.g. consistent cycle threshold (Ct) values with different gene variants. This helps essentially with assay optimization and data (cut-off) interpretation; and iii) absence of major interaction between multiple oligonucleotide pairs simultaneously used in the assay.

In one embodiment of the invention the oligonucleotides have or contain preferably the following sequences:

| Target gene for design of primers | Fw 5'-3' | Sequence | Confirmed target genes |
|---|---|---|---|
| OXA-48 | F_oxa48_003 | TTACTGAACATAAATCACAGG (SEQ ID NO: 1) | |
| | R_oxa48_003 | ATTATTGGTAAATCCTTGCTGCTTATTCTC (SEQ ID NO: 2) | |
| SME | F_sme_006 | CAGATGAGCGGTTCCCTTTATGC (SEQ ID NO: 3) | 1-3 |
| | R_sme_006 | CAGAAGCCATATCACCTAATGTCATACC (SEQ ID NO: 4) | |
| GIM-1 | F_gim_001 | CGAATGGGTTGGTAGTTCTGGATAATAATC (SEQ ID NO: 5) | |
| | R-gim_001 | ATGTGTATGTAGGAATTGACTTTGAATTTAGC (SEQ ID NO: 6) | |
| SIM-1 | F_sim_001 | CTGCTGGGATAGAGTGGCTTAATAC (SEQ ID NO: 7) | |
| | R_sim_001 | TCAATAGTGATGCGTCTCCGATTTC (SEQ ID NO: 8) | |
| VIM | F_vim_03 | GTGTTTGGTCGCATATCGCAAC (SEQ ID NO: 9) | 1-22 |
| | R_vim_03 | GCTGTATCAATCAAAAGCAACTCATC (SEQ ID NO: 10) | |
| SPM | F_spm_001 | CCTACAATCTAACGGCGACCAAG (SEQ ID NO: 11) | |
| | R_spm_001 | AACGGCGAAGAGACAATGACAAC (SEQ ID NO: 12) | |
| GES | F_ges_001 | ACACCTGGCGACCTCAGAGATAC (SEQ ID NO: 13) | 1-10 |
| | R_ges_001 | ACTTGACCGACAGAGGCAACTAATTC (SEQ ID NO: 14) | |
| KPC | F_kpc_001 | CAGCGGCAGCAGTTTGTTGATTG (SEQ ID NO: 15) | 1-7 |
| | R_kpc_001 | CCAGACGACGGCATAGTCATTTG (SEQ ID NO: 16) | |
| IMI-1-3/NMC-A | F_imi1_001 | AAACAAGGGAATGGGTGGAGACTG (SEQ ID NO: 17) | 1-3 + 1 |
| | R_imi1_001 | AAGGTATGCTTTGAATTTGCGTTGAAC (SEQ ID NO: 18) | |
| IMP-10 | F_imp_10 | AATAATGACGCCTATCTAATTGACACTCC (SEQ ID NO: 19) | IMP 1-24 |
| | R_imp_10 | ATTCCACCCGTACTGTCGCTATG (SEQ ID NO:20) | |
| IMP-11,21,22 | F_imp_11 | TGACGCCTATCTGATTGACACTCC (SEQ ID NO: 21) | IMP 1-24 |
| | R_imp_11 | GCTGTCGCTATGGAAATGTGAGG (SEQ ID NO: 22) | |
| OXA-25 | F_oxa25_001 | CCAGTACAAGAAGTTAATTTTGCCGATG (SEQ ID NO: 23) | OXA-25, -26, -40, -24, -72 |
| | R_oxa25_001 | CCCAACCAGTCAACCAACCTACC (SEQ ID NO: 24) | |
| OXA-27 | F_oxa27_001 | ATATTTTACTTGCTATGTGGTTGCTTCTC (SEQ ID NO: 25) | OXA-23, -27 |
| | R_oxa27_001 | TCTCCAATCCGATCAGGGCATTC (SEQ ID NO: 26) | |
| OXA-50 | F_oxa50_001 | AGTGCCCTTCTCCTGCTTTCC (SEQ ID NO: 27) | OXA-50 |
| | R_oxa50_001 | CCTCGTCGGCGGATCTAACC (SEQ ID NO: 28) | |

-continued

| Target gene for design of primers | Fw 5'-3' | Sequence | Confirmed target genes |
|---|---|---|---|
| OXA-51 | F_oxa51_001 | AATTTATTTAACGAAGCACACACTACGG (SEQ ID NO: 29) | OXA-51, -64, -65, -66, -68, -69, -70, -71, -75, -76, -77, -78, -83, -84, -86, -87, -88, -89, -92, -94, -95 |
|  | R_oxa51_001 | GCACGAGCAAGATCATTACCATAGC (SEQ ID NO: 30) |  |
| OXA-55 | F_oxa55_02 | TGTGCTGTGTTATCTGAC (SEQ ID NO: 31) | OXA-55 |
|  | R_oxa55_02 | GTGTTTCTGGACTTCTTTAC (SEQ ID NO: 32) |  |
| OXA-58 | F_oxa58_02 | GACAATTACACCTATACAAGAAG (SEQ ID NO: 33) | OXA-58 |
|  | R_oxa58_02 | CGCTCTACATACAACATCTC (SEQ ID NO: 34) |  |
| OXA-60 | F_oxa60_02 | TTCGACGTTCAAGATTCC (SEQ ID NO: 35) | OXA-60 |
|  | R_oxa60_02 | TTCGAAAGCGGAAATCTC (SEQ ID NO: 36) |  |
| OXA-62 | F_oxa62_02 | TGTCATGCCTGCCCTGCTATC (SEQ ID NO: 37) | OXA-62 |
|  | R_oxa62_02 | ACGAAGTCCACCTGCTCACG (SEQ ID NO: 38) |  |
| CMY-1,10 | F_cmy_01 | CAGGTGCTCTTCAACAAG (SEQ ID NO: 39) | CMY-1, 10, -11 |
|  | R_cmy_01 | CGCCCTCTTTCTTTCAAC (SEQ ID NO: 40) |  |
| SFC-1 | F_sfc_01 | CCTGGTGATGATAGAGATAC (SEQ ID NO41) | SFC-1 |
|  | R_sfc_01 | ATAATCGTTGGCTGTACC (SEQ ID NO:42) |  |

The oligonucleotides have or contain the sequences as presented above except that the following target genes are preferably detected with the following oligonucleotides:

In one preferred embodiment of the invention the following genes, gene families or gene subvariants can be detected in one (first reaction): OXA-48, SME 1-3, GIM-1, VIM

| Target gene for design of primers | Fw 5'-3' | Sequence | Confirmed target genes |
|---|---|---|---|
| OXA-48 | F_oxa48_003 | TTACTGAACATAAATCACAGGGCGTAG (SEQ ID NO: 49) |  |
|  | R_oxa48_003 | ATTATTGGTAAATCCTTGCTGCTTATTCTC (SEQ ID NO: 2) |  |
| OXA-24 group | F_oxa24_02 | ACTTTAGGTGAGGCAATG (SEQ ID NO: 43) | OXA-24, -25, -26, -40, -72 |
|  | R_oxa24_02 | TAACTTCTTGTACTGGTGTAA (SEQ ID NO: 44) |  |
| OXA-51 group with IS-abaI promoter | F_IS51_01 | GTCATAGTATTCGTCGTTAGA (SEQ ID NO: 45) | OXA-51, -64,-65, -66, -68, -69, -70, -71 -75, -76, -77, -78, -83, -84, -86, -87, -88, -89, -92, -94, -95 |
|  | R_IS51_01 | GTAAGAGTGCTTTAATGTTCATA (SEQ ID NO: 46) |  |
| NDM-1 | F_ndm_01 | CGATCAAACCGTTGGAAG (SEQ ID NO: 47) | NDM-1 |
|  | R_ndm_01 | AAGGAAAACTTGATGGAATTG (SEQ ID NO: 48) |  |

1-22, SPM, GES 1-10, KPC 1-7, IMI 1-3/NMC-A, I and/or IMP1-24.

Preferably, in another (second) reaction can be detected the following genes, gene families or gene subvariants: OXA-23 group, OXA-24 group, OXA-51 group with ISabal promoter, OXA-55, OXA-58, OXA-60, OXA-62, CMY-1, -10, -11, SFC-1, NDM-1 and/or SIM-1.

OXA-23 group can detect both OXA-23 and OXA-27. OXA-51 has been replaced with ISAbal-OXA-51 ligation site. OXA-51 can be found in all *Acinetobacter baumannii* bacteria and is clinically significant, when it is in connection with the gene region ISAbal enhancing the reading of the gene. Primers designed for OXA-24 can detect OXA-24, -25, -26, -40, and -72.

The reaction conditions in the multiplex reactions can be the same.

In a preferred embodiment of the invention the amplification reaction is carried out as a PCR reaction by using a PCR program, which comprises a typical two stage gene amplification and real time detection at annealing/extension stage and thereafter analysis of the dissociation temperature. The equipment is preferably Stratagene MxPro 3005P.

| Phase | Temperature ° C. | Duration |
|---|---|---|
| 1. Initial denaturation/activation | 95 | 10 min |
| 2. Denaturation | 95 | 20 s |
| 3. Annealing/extension | 58 | 30 s |
| 4. Repeat stages 2.-3. 30 | | |
| 5. End extension | 58 | 60 s |
| 6. Denaturation | 95 | 30 s |
| 7. Dissociation/melting temperature | 58-95 | automatic (or 5 s) |

Typically the length of the amplification products is about 100-300 bases, with the SIM gene the product length is about 500 bases.

Within the scope of the invention are also embodiments, where the PCR conditions have been slightly modified. It is within the skill of a person skilled in the art to find out conditions, where the temperature is raised with 1, 2 or 3° C. in stages 1 to 8, or the duration of the reaction steps is shortened or lengthened with 1 to 5, or 1 to 3 minutes in stage 1 or with 1 to 5, or 1 to 3 seconds in stages 2 to 8.

The amount of the oligonucleotide primers in the reaction mixture can be equal or the amount of each oligonucleotide can be chosen to be most optimal for the reaction.

The amplification of target nucleic acid sequence in a biological sample is monitored in real time, said method comprising the steps of: amplifying the target sequence by polymerase chain reaction in the presence of a quantity of SYBR™ Green I, said polymerase chain reaction comprising the steps of adding the SYBR™ Green I, a thermostable polymerase, and primers for the target nucleic acid sequence to the biological sample to create an amplification mixture and thermally cycling the amplification mixture between at least a denaturation temperature and an elongation temperature during a plurality of amplification cycles; illuminating the mixture with light at a wavelength absorbed by the SYBR™ Green I in at least a portion of the plurality of amplification cycles; and detecting a fluorescent emission from the SYBR™ Green I following sample illumination said fluorescent emission being related to the quantity of amplified target nucleic acid in the sample. The sample is illuminated and fluorescence is detected as the temperature is increased, to generate a melting curve.

A suitable method for monitoring the amplification of target nucleic acid sequence in real time is described for example in U.S. Pat. No. 6,569,627.

The invention has many advantages. It makes possible to identify quickly strains which threaten the hygiene of hospitals and continuous follow-up. This is only partly possible by using biochemical methods. The use of molecular biology methods alone or in combination with biochemical methods is a remarkable improvement over the prior art.

Unambiguous and accurate knowledge of genetic mechanism makes it possible to use correct treatment, including optimal antibiotic choice (Poirel L et al, Future Microbiol. 2007, 2(5), 501-512).

In particular real time—PCR suits technically excellently to clinical routine diagnostics because it is easy to use and the contamination risk is small (closed system).

In a preferred embodiment of the invention labeled probes are not needed, SYBR Green or EVA Green chemistry is preferable.

As is described in the Example, by using the new high-throughput screening assay an *E. cloacae* harbouring IMI-2 gene was identified. *E. cloacea* with IMI-2 gene has previously been reported apparently only once, in China.

Biochemical methods have been considered insufficient to identify the carbapenem resistance mechanisms (Giske et al, 2009). This invention provides in its preferred embodiment an identification method based on Real-Time multiplex PCR for screening of clinically significant carbapenem resistance genes (carbapenemase genes), in particular among Enterobacteriaceae, *Acinetobacter* sp. and *Pseudomonas* sp. An advantage of the method and kit according to this invention is that the method allows detection of new mutations and variations, for example OXA-48 variants OXA-163 and OXA-181, the sequences of which differ crucially (ad 9%) from the previously known sequences. Traditional probe—based test are sensitive even to a change of one base within the probed area, and therefore such tests easily give false negative results. The rate of evolution of the carbapenem resistant bacteria is very rapid. To illustrate this: at the time the inventors began to develop the current test one NDM variation was known, today six NDM point mutated variations are known. All this mutations are detectable with the current test, while not necessarily with a probebased test.

The following numbered paragraphs each succinctly define one or more exemplary variations of the invention:
1. A method for detecting carbapenemase genes in a biological sample, which comprises the steps:
   carrying out an amplification reaction in the presence of a nucleic acid template from the biological sample and primers, said primers being 15 to 50 nucleotides long and having at least part or comprising a nucleotide sequence selected from the group comprising SEQ ID NOS: 1-49;
   analyzing the dissociation curves of the products, and determining the presence of polynucleotides responsible of carbapenemase genes causing resistance indicating that the biological sample comprises carbapenemase genes causing carbapenem resistance.
2. The method according to paragraph 1, wherein the method comprises carrying out the amplification as a polymerase chain reaction in the presence of a nucleic acid template from the biological sample, polymerase enzyme and PCR buffer, a mixture of nucleoside triphosphate monomers and PCR primers.

3. The method according to paragraph 1 or 2, wherein the method comprises that the products of the reaction are sequenced.
4. The method according to any one of paragraph 1 to 3, wherein the method comprises primer pairs selected from the group comprising
a first oligonucleotide primer comprising SEQ ID NO: 1 or 49 and a second oligonucleotide primer SEQ ID NO:2;
a first oligonucleotide primer comprising SEQ ID NO: 3 and a second oligonucleotide primer SEQ ID NO:4;
a first oligonucleotide primer comprising SEQ ID NO: 5 and a second oligonucleotide primer SEQ ID NO:6;
a first oligonucleotide primer comprising SEQ ID NO: 7 and a second oligonucleotide primer SEQ ID NO:8;
a first oligonucleotide primer comprising SEQ ID NO: 9 and a second oligonucleotide primer SEQ ID NO:10;
a first oligonucleotide primer comprising SEQ ID NO: 11 and a second oligonucleotide primer SEQ ID NO:12;
a first oligonucleotide primer comprising SEQ ID NO: 13 and a second oligonucleotide primer SEQ ID NO:14;
a first oligonucleotide primer comprising SEQ ID NO: 15 and a second oligonucleotide primer SEQ ID NO:16;
a first oligonucleotide primer comprising SEQ ID NO: 17 and a second oligonucleotide primer SEQ ID NO:18;
a first oligonucleotide primer comprising SEQ ID NO: 19 and a second oligonucleotide primer SEQ ID NO:20;
a first oligonucleotide primer comprising SEQ ID NO: 21 and a second oligonucleotide primer SEQ ID NO:22;
a first oligonucleotide primer comprising SEQ ID NO: 23 and a second oligonucleotide primer SEQ ID NO:24;
a first oligonucleotide primer comprising SEQ ID NO: 25 and a second oligonucleotide primer SEQ ID NO:26;
a first oligonucleotide primer comprising SEQ ID NO: 27 and a second oligonucleotide primer SEQ ID NO:28;
a first oligonucleotide primer comprising SEQ ID NO: 29 and a second oligonucleotide primer SEQ ID NO:30;
a first oligonucleotide primer comprising SEQ ID NO: 31 and a second oligonucleotide primer SEQ ID NO:32;
a first oligonucleotide primer comprising SEQ ID NO: 33 and a second oligonucleotide primer SEQ ID NO:34;
a first oligonucleotide primer comprising SEQ ID NO: 35 and a second oligonucleotide primer SEQ ID NO:36;
a first oligonucleotide primer comprising SEQ ID NO: 37 and a second oligonucleotide primer SEQ ID NO:38;
a first oligonucleotide primer comprising SEQ ID NO: 39 and a second oligonucleotide primer SEQ ID NO:40;
a first oligonucleotide primer comprising SEQ ID NO: 41 and a second oligonucleotide primer SEQ ID NO:42;
a first oligonucleotide primer comprising SEQ ID NO: 43 and a second oligonucleotide primer SEQ ID NO:44;
a first oligonucleotide primer comprising SEQ ID NO: 45 and a second oligonucleotide primer SEQ ID NO:46;
a first oligonucleotide primer comprising SEQ ID NO: 47 and a second oligonucleotide primer SEQ ID NO:48.
5. The method according to any one of paragraphs 1 to 4, wherein the reaction is carried out by real time PCR, preferably based on SYBR® Green chemistry identification.
6. The method according to any one of paragraphs 1 to 5, wherein the reaction is carried out on two separate multiplex reactions having commonly compatible amplification conditions.
7. The method according to any one of paragraphs 1 to 6, wherein the first multiplex reaction is able to detect one or more gene or gene families selected from the group comprising:
KPC 1-7, OXA-48, VIM 1-22, GES 1-10, and IMP1-24 within a single reaction.
8. The method according to any one of paragraphs 1 to 7, wherein the first multiplex reaction is able to detect one or more gene or gene families selected from the group comprising:
KPC 1-7, OXA-48, VIM 1-22, GES 1-10, IMP 1-24, SME 1-3, GIM-1, SPM, IMI 1-3/NMC-A, within a single reaction.
9. The method according to any one of paragraphs 1 to 7, wherein the first multiplex reaction is able to detect one or more gene or gene families selected from the group comprising:
VIM 1-22, IMP 1-24, OXA-48, KPC 1-7, GES 1-10, SPM, NMC-A, IMI 1-2, SME 1-3, GIM-1, and SIM-1 within a single reaction.
10. The method according to any one of claims paragraph 7 to 9, wherein the first multiplex reaction is able to detect at least one of each of the genes or gene families within a single reaction.
11. The method according to any one of claims paragraph 7 to 10, wherein the first multiplex reaction is able to detect all the genes, gene families and/or gene subvariants within a single reaction.
12. The method according to any one of paragraphs 1 to 11, wherein the second multiplex reaction is able to detect one or more genes or gene families selected from the group comprising:
OXA-24, -25, 26, -40, -72, OXA-23, -27, OXA-50, OXA-51, 64-71, 75-78, 83-89, -92, -94, -95, OXA-55, OXA-58, OXA-60, OXA-62, SFC-1, and CMY-1, -10, -11 within a single reaction.
13. The method according to any one of paragraphs 1 to 11, wherein the second multiplex reaction is able to detect one or more genes or gene families selected from the group comprising:
OXA-23 group, OXA-24 group, OXA-51 group with ISabal promoter, OXA-58, and NDM-1.
14. The method according to any one of paragraphs 1 to 11, wherein the second multiplex reaction is able to detect one or more genes or gene families selected from the group comprising:
OXA-23 group, OXA-24 group, OXA-51 group with ISabal promoter, OXA-55, OXA-58, OXA-60, OXA-62, CMY-1, -10, SFC-1, NDM-1, and SIM-1.
15. The method according to any one of paragraphs 12 to 14, wherein the second multiplex reaction is able to detect at least one of each of the genes or gene families within a single reaction.
16. The method according to any one of paragraphs 12 to 15, wherein the second multiplex reaction is able to detect all the genes, gene families and/or gene subvariants within a single reaction.
17. The method according to any one of paragraphs 12 to 16, wherein the second multiplex reaction is able to detect at least one of each of the OXA genes or gene families in one reaction, preferably all the OXA genes, gene families and/or gene subvariants within a single reaction.
18. A kit comprising a set of primer pairs for identifying carbapenemase genes causing carbapenem resistance in bacteria, said primers being 15 to 50 nucleotides long and having at least part or comprising a nucleotide sequence selected from the group comprising SEQ ID NOS: 1-49 or a modified form thereof.
19. The kit according to paragraph 12, wherein the kit comprises a primer pair selected from the group comprising a first oligonucleotide primer comprising SEQ ID NO: 1 or 49 and a second oligonucleotide primer SEQ ID NO:2;
a first oligonucleotide primer comprising SEQ ID NO: 3 and a second oligonucleotide primer SEQ ID NO:4;
a first oligonucleotide primer comprising SEQ ID NO: 5 and a second oligonucleotide primer SEQ ID NO:6;
a first oligonucleotide primer comprising SEQ ID NO: 7 and a second oligonucleotide primer SEQ ID NO:8;
a first oligonucleotide primer comprising SEQ ID NO: 9 and a second oligonucleotide primer SEQ ID NO:10;
a first oligonucleotide primer comprising SEQ ID NO: 11 and a second oligonucleotide primer SEQ ID NO:12;
a first oligonucleotide primer comprising SEQ ID NO: 13 and a second oligonucleotide primer SEQ ID NO:14;
a first oligonucleotide primer comprising SEQ ID NO: 15 and a second oligonucleotide primer SEQ ID NO:16;
a first oligonucleotide primer comprising SEQ ID NO: 17 and a second oligonucleotide primer SEQ ID NO:18;
a first oligonucleotide primer comprising SEQ ID NO: 19 and a second oligonucleotide primer SEQ ID NO:20;
a first oligonucleotide primer comprising SEQ ID NO: 21 and a second oligonucleotide primer SEQ ID NO:22;
a first oligonucleotide primer comprising SEQ ID NO: 23 and a second oligonucleotide primer SEQ ID NO:24;
a first oligonucleotide primer comprising SEQ ID NO: 25 and a second oligonucleotide primer SEQ ID NO:26;
a first oligonucleotide primer comprising SEQ ID NO: 27 and a second oligonucleotide primer SEQ ID NO:28;
a first oligonucleotide primer comprising SEQ ID NO: 29 and a second oligonucleotide primer SEQ ID NO:30;
a first oligonucleotide primer comprising SEQ ID NO: 31 and a second oligonucleotide primer SEQ ID NO:32;
a first oligonucleotide primer comprising SEQ ID NO: 33 and a second oligonucleotide primer SEQ ID NO:34;
a first oligonucleotide primer comprising SEQ ID NO: 35 and a second oligonucleotide primer SEQ ID NO:36;
a first oligonucleotide primer comprising SEQ ID NO: 37 and a second oligonucleotide primer SEQ ID NO:38;
a first oligonucleotide primer comprising SEQ ID NO: 39 and a second oligonucleotide primer SEQ ID NO:40;
a first oligonucleotide primer comprising SEQ ID NO: 41 and a second oligonucleotide primer SEQ ID NO:42;
a first oligonucleotide primer comprising SEQ ID NO: 43 and a second oligonucleotide primer SEQ ID NO:44;
a first oligonucleotide primer comprising SEQ ID NO: 45 and a second oligonucleotide primer SEQ ID NO:46;
a first oligonucleotide primer comprising SEQ ID NO: 47 and a second oligonucleotide primer SEQ ID NO:48.

14. The kit according to paragraph 12 or 13, wherein the kit comprises primer pairs for identifying one or more of the genes or gene families or gene subvariants selected from the group comprising:
KPC 1-7, OXA-48, VIM 1-22, GES 1-10, and IMP1-24 within a single reaction.

15. The kit according to any one of paragraphs 12 to 14, wherein the kit comprises primer pairs for identifying one or more of the genes or gene families or gene subvariants selected from the group comprising:
KPC 1-7, OXA-48, VIM 1-22, GES 1-10, IMP 1-24, SME 1-3, GIM-1, SPM, IMI 1-3/NMC-A, within a single reaction.

16. The kit according to any one of paragraphs 12 to 14, wherein the kit comprises primer pairs for identifying one or more of the genes or gene families or gene subvariants selected from the group comprising:
VIM 1-22, IMP 1-24, OXA-48, KPC 1-7, GES 1-10, SPM, NMC-A, IMI 1-2, SME 1-3, GIM-1, and SIM-1 within a single reaction.

17. The kit according to any one of paragraphs 12 to 16, wherein the kit comprises primer pairs for a first multiplex reaction able to detect at least one of each of the genes or gene families within a single reaction.

18. The kit according to any one of paragraphs 12 to 17, wherein the kit comprises primer pairs for a first multiplex reaction able to detect all the genes, gene families and/or gene subvariants within a single reaction.

19. The kit according to any one of paragraphs 12 to 18, wherein the second multiplex reaction is able to detect one or more of the genes or gene families or gene subvariants selected from the group comprising:
OXA-24, -25, 26, -40, -72, OXA-23, -27, OXA-50, OXA-51, 64-71, 75-78, 83-89, -92, -94, -95, OXA-55, OXA-58, OXA-60, OXA-62, SFC-1, and CMY-1, -10, -11 within a single reaction.

20. The kit according to any one of paragraphs 12 to 18, wherein the second multiplex reaction is able to detect one or more of the genes or gene families or gene subvariants selected from the group comprising:
OXA-23 group, OXA-24 group, OXA-51 group with ISabal promoter, OXA-58, and NDM-1 within a single reaction.

21. The kit according to any one of paragraphs 12 to 20, wherein the second multiplex reaction is able to detect one or more of the genes or gene families or gene subvariants selected from the group comprising:
OXA-23 group, OXA-24 group, OXA-51 group with ISabal promoter, OXA-55, OXA-58, OXA-60, OXA-62, CMY-1, -10, SFC-1, NDM-1, and SIM-1.

22. The kit according to any one of paragraphs 12 to 21, wherein the kit comprises primer pairs for a second multiplex reaction able to detect at least one of each of the genes or gene families within a single reaction.

23. The kit according to any one of paragraphs 12 to 22, wherein the kit comprises primer pairs for a second multiplex reaction able to detect all the genes, gene families and/or gene subvariants within a single reaction.

24. The kit according to any one of paragraphs 12 to 23, wherein the kit comprises primer pairs for a second multiplex reaction able to detect at least one of each of the OXA geneor gene families in a single reaction, preferably all the OXA genes, gene families and/or gene subvariants within a single reaction.

25. An oligonucleotide primer for identifying carbapenem resistant genes, wherein the oligonucleotide has at least part or comprises a nucleotide sequence selected from the group comprising SEQ ID NOS: 1-49 or modified form thereof.

26. An oligonucleotide selected from the group comprising SEQ ID NOS: 1-49.

27. An arrangement for identifying carbapenemase genes, which comprises a first and a second multiplex reaction, wherein in the first multiplex reaction is detected one or more or all of the genes or gene families and/or gene subvariants selected from the group comprising
KPC 1-7, OXA-48, SME 1-3, GIM-1, VIM 1-22, SPM, GES 1-10, IMP 1-24, NMC-A/IMI 1-2, and SIM-1; or
KPC 1-7, OXA-48, SME, GIM-1, VIM 1-22, SPM, GES 1-10, IMP 1-24 and IMI 1-3/NMC-A; and
in the second multiplex reaction is detected one or more or all of the genes or gene families and/or subvariants selected from the group comprising
OXA-24, -25, 26, -40, -72, OXA-23, -27, OXA-50, OXA-51, 64-71, 75-78, 83-89, -92, -94, -95, OXA-55, OXA-58, OXA-60, OXA-62; or selected from the group comprising OXA-23 group, OXA-24 group, OXA-51 group with ISabal promoter, OXA-55, OXA-58, OXA-60, OXA-62, NDM-1, and SIM-1.

28. The arrangement according to paragraph 27, wherein in the second multiplex reaction is further detected one or more or all of the genes or gene families or subvariants of SFC-1, CMY-1, -10, -11.

29. A method for detecting carbapenemase genes in a biological sample, which comprises the steps:
carrying out an amplification reaction in the presence of a nucleic acid template from the biological sample, and primers, said primers being 15 to 50 nucleotides long and having at least part or comprising a nucleotide sequence selected from the group comprising SEQ ID NOS: 15 and 16, 1, 49, 2, 9, 10, 13, 14, 19, 20, 21, 22, or modified sequences of said sequences;
analyzing the dissociation curves of the products, and determining the presence of KPC, OXA-48, VIM, GES, and/or IMP genes or their subvariants responsible of carbapenem resistance indicating that the biological sample comprises carbapenemase genes causing carbapenemase resistance in bacteria.

30. The method according to paragraph 29, wherein said primer sequence is capable of detecting the target polynucleotide sequence, carbapenemase gene.

31. The method according to paragraph 29 or 30, wherein the method further comprises primers being 15 to 50 nucleotides long and having at least part or comprising a nucleotide sequence selected from the group comprising SEQ ID NOS: 3, 4, 5, 6, 7, 8, 11, 12, 17 and 18, or a modified form thereof for determining the presence of SME, GIM-1, SIM-1, SPM, NMC-A and/or IMI genes or their subvariants.

32. The method according to any one of paragraphs 29 to 30, wherein the method further comprises primers being 15 to 50 nucleotides long and having at least part or comprising a nucleotide sequence selected from the group comprising SEQ ID NOS: 3, 4, 5, 6, 11, 12, 17 and 18, or a modified form thereof for determining the presence of SME, GIM-1, SPM and/or IMI /NMC-A.

33. The method according to any one of paragraphs 29 to 32, wherein the method further comprises primers being 15 to 50 nucleotides long and having at least part or comprising a nucleotide sequence selected from the group comprising SEQ ID NOS: 23, 24, 25, 26, 27, 28, 29, 30, 31, 32, 33 and 34, 35, 36, 37 , 38, 39, 40, 41 and 42, or a modified form thereof for determining the presence of one or more of OXA -24, 25, 26, -40, -72, OXA-23, -27, OXA-50, OXA-51, 64-71, 75-78, 83, 84, 86-89, -92, -94, -95, OXA-55, OXA-58, OXA-60, OXA-62, SFC-1, and/or CMY-1-10 genes or their subvariants.

34. The method according to any one of paragraphs 29 to 32, wherein the method further comprises primers being 15 to 50 nucleotides long and having at least part or comprising a nucleotide sequence selected from the group comprising SEQ ID NOS: 25, 26, 43, 44, 45, 46, 31, 32, 33, 34, 35, 36, 37, 38, 39, 40, 41, 42, 47 and 48, or a modified form thereof for determining the presence of one or more of OXA-23 group, OXA-24 group, OXA-51 group with ISabal promoter, OXA-55, OXA-58, OXA-60, OXA-62, CMY-1, -10, SFC-1, NDM-1, and/or SIM-1 genes or their subvariants.

35. The method according to any one of paragraphs 29 to 34, wherein the reaction is carried out on two separate multiplex reactions having commonly compatible amplification conditions.

36. A kit comprising a set of primer pairs for identifying carbapenemase genes, said primers being 15 to 50 nucleotides long and having at least part or comprising a nucleotide sequence selected from the group comprising SEQ ID NOS: 15, 16, 1 or 49, 2, 9, 10, 13, 14, 19, 20, 21 and 22, or a modified form thereof for determining the presence of KPC, OXA-48, VIM, GES, and/or IMP genes or their subvariants .

37. The kit according to paragraph 36, wherein the kit further comprises primers being 15 to 50 nucleotides long and having at least part or comprising a nucleotide sequence selected from the group comprising SEQ ID NOS: 3, 4, 5, 6, 7, 8, 11, 12, 17 and 18, or a modified form thereof for determining the presence of SME, GIM-1, SIM-1, SPM, NMC-A and/or IMI genes or their subvariants.

38. The kit according to paragraph 36 or 37, wherein the kit further comprises primers being 15 to 50 nucleotides long and having at least part or comprising a nucleotide sequence selected from the group comprising 3, 4, 5, 6, 11, 12, 17 and 18, or a modified form thereof for determining the presence of SME, GIM-1, SPM and/or IMI 1-3/NMC-A.

39. The kit according to any one of paragraphs 36 to 38, wherein the kit further comprises primers being 15 to 50 nucleotides long and having at least part or comprising a nucleotide sequence selected from the group comprising 23, 24, 25, 26, 27, 28, 29, 30, 31, 32, 33 and 34, 35, 36, 37 , 38, 39, 40, 41 and 42, or a modified form thereof for determining the presence of OXA -24, 25, 26, -40, -72, OXA-23, -27, OXA-50, OXA-51, 64-71, 75-78, 83, 84, 86-89, -92, -94, -95, OXA-55, OXA-58, OXA-60, OXA-62, SFC-1, and/or CMY-1-10 genes or their subvariants.

40. The kit according to any one of paragraphs 36 to 38, wherein the kit further comprises primers being 15 to 50 nucleotides long and having at least part or comprising a nucleotide sequence selected from the group 25, 26, 43, 44, 45, 46, 31, 32, 33, 34, 35, 36, 37, 38, 39, 40, 41, 42, 47 and 48, or a modified form thereof for determining the presence of one or more OXA-23 group, OXA-24 group, OXA-51 group with ISabal promoter, OXA-55, OXA-58, OXA-60, OXA-62, CMY-1, -10, SFC-1, NDM-1, and SIM-1 genes or their subvariants.

41. An oligonucleotide for identifying carbapenemase genes, wherein the oligonucleotide comprises a nucleotide sequence selected from the group comprising SEQ ID NOS: 15, 16, 1, 49, 2, 9, 10, 13, 14, 19, 20, 21 and 22.

42. An arrangement for identifying carbapenemase genes, which comprises a first and a second multiplex reaction, wherein in the first multiplex reaction is detected one or more or all of the genes, gene families and/or gene subvariants of KPC, OXA-48, VIM, GES, and/or IMP within a single reaction; said detection being carried out by using primers being 15 to 50 nucleotides long and having at least part or comprising a nucleotide sequence selected from the group comprising SEQ ID NOS: 15, 16, 1, 2, 9, 10, 13, 14, 19, 20, 21 and 22 or a modified form thereof .

43. The arrangement according to paragraph 42, wherein in the second multiplex reaction is detected one or more or all of the genes, gene families and/or subvariants of OXA-23 group, OXA-24 group, OXA-51 group with ISabal promoter, OXA-58, and/or NDM-1, within a single reaction, said detection being carried out by using primers being 15 to 50 nucleotides long and having at least part or comprising a nucleotide sequence selected from the group comprising SEQ ID NOS: 24, 25, 43, 44, 45, 46, 47, 33, 34 and 48 or a modified form thereof.

The invention is now described by example of the following non-limiting examples. One skilled in the art would realize that modifications may be done without diverting from the spirit of the invention.

EXAMPLES

Example 1

Methods

The Real-Time PCR assay design was divided in two multiplex reactions. The first multiplex was designed to detect VIM 1-22, IMP 1-24, OXA-48, KPC 1-7, GES 1-10, SPM, NMC-A, IMI 1-2, SME 1-3, GIM-1, and SIM-1 genes. The other multiplex was designed for OXA genes with carbapenemase properties only, including OXA-24, -25, 26, -40, -72, OXA-23, -27, OXA-50, OXA-51, 64-71, 75-78, 83-89, -92, -94, -95, OXA-55, OXA-58, OXA-60, and OXA-62. SYBR Green chemistry was chosen to allow numerous genes to be detected within single reaction. A melting curve analysis was used to preliminarily identify putative molecular mechanism of positive samples, which were confirmed with sequencing with reference primers. This assay was used to screen putative ESBL strains systematically. Moreover, the screening assay is part of routine diagnostics to screen putative Enterobacteriaceae species with reduced susceptibility (meropenem disk diameter <23 mm), or reduced MIC (I/R) to meropenem, imipenem or ertapenem according to NLSI standards.

Results

Over 250 putative ESBL strains were systemically screened to evaluate prevalence of carbapenemase producing strains, but they were not detected. In contrast, a highly carbapenem resistant *Enterobacter cloacae* strain harbouring IMI-2 gene was isolated from a patient in intensive care unit. The IMI-2 positive strain was highly resistant to meropenem (MIC>32), imipenem (MIC>32) and ertapenem (MIC>256), but interestingly not, however, resistant to third generation cephalosporins, or trimetoprim/sulfa. In addition, the assay has succesfully used to identify more than thirty clinical *Acinetobacter* isolates harbouring OXA-23 group and/or OXA-51 group, or VIM-2 carbapenemases.

Example 2

The methods as described in Example 1 were repeated to detect in the first multiplex reaction OXA-48, SME, GIM-1, VIM, SPM, GES, KPC, IMI 1-3/NMC-A, IMP-10, IMP-11, and in the second multiplex reaction OXA-23 group, OXA-24 group, OXA-51 group with ISabal promoter, OXA-55, OXA-58, OXA-60, OXA-62, CMY-1, -10, SFC-1, NDM-1, and SIM-1.

In these experiments were found four *Klebsiella pneumoniae* strains with KPC gene, one *E. coli* strain with OXA-48, three *Pseudomonas aeruginosa* strains with GES, and six *Pseudomonas aeruginosa/putida* strains with IMP gene. Also more than fifty *Acinetobacter baumannii* complex strains with different combinations of OXA-23, OXA-24, OXA-58 genes were found.

Example 3

To detect carbapenemase genes in Enterobacteriaceae, *Pseudomonas* sp. and *Acinetobacter* sp., we developed a simple multiplex Real-Time PCR potentially detecting >100 different carbapenemase genes or their variants from culture isolates. The assay comprise from multiplex PCR divided in two reactions, Multiplex 1 detecting IMP, IMI/NMC-A, KPC, GES, VIM, OXA-48 group (incl. OXA-163, -181), GIM-1, SPM-1, and SME.

TABLE 1 illustrates the strains detected with the first multiplex detection.

| Species | Strain ID | Gene | Gene group | Typical Ct (50 ng/µl) | T(m) |
|---|---|---|---|---|---|
| Ps. aeruginosa | T-105312 | IMP-15 | IMP | 15 | 77 |
| E. cloacae | T-64586 | IMI-2 | IMI, NMC-A | 14 | 78 |
| Kl. pneumoniae | JK78 | KPC-2 | KPC | 17 | 87 |
| Kl. pneumoniae | JK241 | GES-1 | GES | 23 | 84 |
| Kl. pneumoniae | 293 | VIM-1 | VIM | 17 | 81 |
| E. coli | 301 | OXA-48 | OXA-48, -181 | 15 | 75 |
| Ps. aeruginosa | 1078 | GIM-1 | GIM-1 | 16 | 80 |
| Ps. aeruginosa | 1081 | SPM-1 | SPM-1 | 16 | 80 |
| E. coli* | #925 | SME | SME | 11 | 77 |

*gene construct plasmid in E. coli

Multiplex 2 detecting OXA-24/40 group, OXA-23 group, ISAba1-OXA51 group, OXA-58, CMY-1, 10, SFC, NDM, and SIM. In addition, a subset of genes including OXA-48 group, KPC, VIM and NDM has been successfully tested in one multiplex reaction from stool sample extracted DNA. The technical separation capacity is shown in FIGS. 3 and 4.

TABLE II

Illustrates the strains detected with the second multiplex assay.

| Species | Isolate ID | Gene | Gene group | Typical Ct (50 ng/µl) | T(m) |
|---|---|---|---|---|---|
| Acinetob. -laji | T-102113 | OXA-25 | OXA-24/40-perhe | 17 | 79 |
| Acinetob. -laji | T-91841 | OXA-27 | OXA-23-perhe | 22 | 78 |
| Acinetob. -laji | T-108360 | ISaba1 | Isaba1-OXA51 | 19 | 72 |
| E. coli* | #166 | OXA-58 | OXA-58 | 15 | 76 |
| E. coli* | #924 | CMY-10 | CMY-1, 10 | 16 | 88 |
| E. coli* | #160 | SFC | SFC | 16 | 81 |
| Kl. Pneumoniae | SK116 | NDM-1 | NDM | 18 | 87 |
| Acinetob. -laji | SK114 | SIM | SIM | 21 | 80 |

*gene construct plasmid in E. coli

Example 4

The test according to this invention has been developed for several years for clinical laboratory use. During the development period, the inventors designed tens of oligonucleotide primers and have tested several versions to find optimally amplified pairs in combination with the other oligonucleotides in multplex reaction. The oligonucleotides of this invention do not have undesired interference with each other. The validation material for clinical use includes 1666 putative carbapenemase producing strains screened according to EUCAST criteria. In addition 74 MDR *Acinetobacter baumannii* strains has been tested and confirmed by reference methods, 249 consecutive ESBL strains, 13 targeted stool isolates from travellers returning from Greece, Israel and USA, 60 different Enterobacteriaceae and other Gram negative clinical isolates tested for specificity. The analytical sensitivity of the test is 100% (reference PCR, separate independent analysis in national reference center, including imipenem hydrolysis assay). The specificity is 100% (60 different Gram negative clinical isolates), repeatability is 100%, re-producibility is 100%, analytical ranged is 1-30 cycles. The test is qualitative with analytical sensitivity of approximately 0.005 ng/µl (KPC), 0.05 ng/µl (NDM-1).

Table 3 below illustrates Enterobacteriacae and Pseudomonas sp. strains identified with the test of the current invention and the underlying mechanisms of the resistance.

| Identification | Mechanism |
|---|---|
| E. cloacae | IMI-2 |
| E. cloacae | IMI-1 |
| E. cloacae | NMC-A |
| E. coli | OXA-48 |
| E. coli | OXA-118 (OXA-48 variant) |
| K. pneumoniae | KPC-2 |
| K. pneumoniae | KPC-2 |
| K. pneumoniae | KPC-2 |
| K. pneumoniae | KPC-2 |
| K. pneumoniae | KPC-2 |
| K. pneumoniae | GES-4/5 |
| K. pneumoniae | OXA-48 |
| K. pneumoniae | OXA-181 (OXA-48 variant) |
| K. pneumoniae | VIM-2 |
| K. pneumoniae | VIM-2 |
| K. pneumoniae | VIM-2 |
| K. pneumoniae | NDM-1 |
| K. pneumoniae | NDM-1 |
| E. coli | NDM-1 |
| P. aeruginosa | VIM-2 |
| P. aeruginosa | VIM-2 |
| P. aeruginosa | IMP-15 |
| P. aeruginosa | IMP-15 |
| P. aeruginosa | IMP-15 |
| P. aeruginosa | IMP-15 |
| P. aeruginosa | IMP-15 |

To facilitate prompt clinical screening of putative carriers of carbapenemase producing strains, a direct stool variant was developed for the genes with highest epidemiological relevance, including KPC, OXA-48, VIM and NDM. This variant of the assay is especially significant in the areas with high prevalence of carbapenemase strains as most hospitals have limited capacity for patient isolation facilities. One colony of strains harbouring one of these variants was inoculated in one milliliter of app. 10% stool sample suspension to demonstrate the practical performance. The results (not shown) were technically very good and well in line with the data obtainded from culture isolates.

LITERATURE

1. Queenan A M, Bush K. Carbapenemases: the Versatile β-Lactamases, *Clinical Microbiology Reviews,* 2007 20(3), 440-458.
2. Poirel L, Pitout J D, Nordman P. Carbapenemases: molecular diversity and consequences, *Future Microbiol.* 2007 2(5), 501-512.
3. Giske C G, Redefining extended-spectrum {beta}-lactamases: balancing science and clinical need. *J Antimicrob Chemother.* 2009 63(1), 1-4. Epub 2008 Oct. 28.

What is claimed is:

1. A method for simultaneously detecting a presence or an absence of a multitude of carbapenemase genes in a biological sample, said method comprising the steps of:
   a) carrying out an amplification reaction of a multitude of IMP genes, a multitude of KPC genes, and at least one of VIM, GES, and OXA-48 genes using:
      (i) a first set of primer pairs consisting of at least one primer pair selected from primer pairs of a forward primer SEQ ID NO:19 and reverse primer SEQ ID NO:20; and a forward primer SEQ ID NO:21 and a reverse primer SEQ ID NO:22;
      (ii) a second set of primer pairs consisting of forward primer SEQ ID NO:15 and a reverse primer SEQ ID NO:16;
      (iii) a third set of primer pairs consisting of at least one primer pair selected from the primer pairs of forward primer SEQ ID NO:9 and reverse primer SEQ ID NO:10; forward primer SEQ ID NO: 13 and reverse primer SEQ ID NO:14; and forward primer SEQ ID NO: 1 or SEQ ID NO:49 and reverse primer SEQ ID NO:2;
   wherein the first set of primer pairs are for targeting multitude of IMP genes comprising at least variants IMP 1-24, the second set of primer pairs is for targeting multitude KPC genes comprising at least variants KPC1-7, and the third set of primer pairs is for targeting at least one of VIM, GES and OXA-48 genes;
- b) creating dissociation curves of the amplification products, said products being 100-300 bases long, and analyzing the dissociation curves, and
- c) determining the presence or absence of IMP and KPC genes, and at least one of VIM, GES, and OXA-48 genes, wherein the presence indicates that the biological sample comprises carbapenemase genes causing carbapenem resistance in bacteria.

2. The method according to claim 1, wherein the third set of primer pairs consists of the primer pair SEQ ID NO: 9 and 10, SEQ ID NO: 13 and 14 and SEQ ID NO: 1 and 2.

3. A multiplex reaction kit for simultaneously detecting from a biological sample more than one carbapenemase gene causing carbapenem resistance in bacteria, said kit comprising:
- a thermostable polymerase;
- a nucleic acid binding fluorescent dye capable of binding to amplified products; and
- a set of primer pairs consisting of primers having melting temperature suitable for real time PCR and not interfering with each other in a multiplex reaction, wherein the primer pairs are SEQ ID NO: 15 and 16 for detection of multitude of KPC genes comprising at least KPC 1-7 variants, SEQ ID NO:1 and 2 and/or SEQ ID NO: 49 and 2 for detection of OXA-48 genes, SEQ ID NO: 9 and 10 for detection of VIM genes comprising at least VIM 1-22 variants, SEQ ID NO: 13 and 14 for detection of GES genes comprising at least GES 1-10 variants, and SEQ ID NO: 19 and 20, and/or SEQ ID NO: 21 and 22 for detection of IMP genes comprising at least IMP1-24 variants.

4. The kit according to claim 3, wherein the primer pairs are SEQ ID NO: 19 and 20; SEQ ID NOs 15 and 16, SEQ ID NO: 1 and 49, and SEQ ID NO:9 and 10.

5. A multiplex reaction kit for simultaneously detecting from a biological sample more than one carbapenemase gene causing carbapenem resistance in bacteria, said kit comprising:
- a thermostable polymerase;
- a nucleic acid binding fluorescent dye; and
- a set of primer pairs consisting of primers having melting temperature suitable for real time PCR and not interfering with each other in a multiplex reaction, wherein the primers of the primer pairs are SEQ ID NOS: 15 and 16 for detection of multitude of KPC genes comprising at least KPC 1-7 variants; SEQ ID NO: 1 and 2 or SEQ ID NO: 49 and SEQ ID NO:2 for detection of OXA-48 genes; SEQ ID NO: 9 and 10 for detection of VIM genes comprising at least VIM 1-22 variants; and SEQ ID NO: 47 and 48 for detection for NDM-1 genes.

6. A method for identifying simultaneously more than one carbapenemase gene causing carbapenem resistance in bacteria, said method comprising the steps of:
- a) providing a biological sample;
- b) preparing a first amplification mixture comprising the biological sample, thermostable polymerase, nucleic acid binding fluorescent dye and a first set of primer pairs;
- c) conducting a first multiplex reaction, wherein more than one of the genes, selected from the group consisting of KPC genes comprising at least KPC 1-7 variants, OXA-48, VIM, GES, and IMP genes, comprising at least IMP 1-22 variants, are simultaneously detectable, wherein detection is being carried out by using the first set of primer pairs where the primer pairs are SEQ ID NOS: 15 and 16; SEQ ID NO: 1 or 49 and SEQ ID NO:2; SEQ ID NO: 9 and SEQ ID NO: 10; SEQ ID NO: 13 and SEQ ID NO: 14 ; SEQ ID NO:19 and SEQ ID NO: 20, and SEQ ID NO: 21 and SEQ ID NO: 22;
- d) preparing a second amplification mixture comprising the biological sample, thermostable polymerase, nucleic acid binding fluorescent dye and a second set of primer pairs;
- e) conducting a second multiplex reaction wherein more than one of the genes, selected from KPC genes comprising at least KPC 1-7 variants, OXA-48, and at least one of VIM and NDM-1 genes are simultaneously detectable, wherein the detection is being carried out by using the second set of primer pairs where the primer pairs are SEQ ID NO: 15 and 16; SEQ ID NO: 1 or 49 and 2; SEQ ID NO: 9 and 10; and SEQ ID NO: 47 and 48.

7. The method according to claim 6, wherein the first primer pairs are SEQ ID NO: 15 and SEQ ID NO:16; SEQ ID NO:1 or 49 and SEQ ID NO: 2; SEQ ID NO: 9 and 10, and SEQ ID NO: 19 and 20, and the second primer pairs comprise SEQ ID NO: 47 and 48.

8. A method for identifying simultaneously more than one carbapenemase gene causing carbapenem resistance in bacteria, said method comprising the steps of:
- a) providing a biological sample:
- b) preparing an amplification mixture comprising the biological sample;
- thermostable polymerase, nucleic acid binding fluorescent dye and a set of primer pairs; and
- c) conducting a multiplex reaction, wherein in the multiplex reaction a multitude of KPC genes comprising at least KPC 1-7 variants, OXA-48 and a multitude of VIM genes comprising at least VIM 1-22 variants, are simultaneously detectable, wherein detection is carried out by using primer pairs SEQ ID NOS: 15 and 16; SEQ ID NO: 1 or 49 and 2; SEQ ID NO: 9 and 10; and SEQ ID NO: 47 and 48.

* * * * *

SEQUENCE LISTING

```
<160> NUMBER OF SEQ ID NOS: 49

<210> SEQ ID NO 1
<211> LENGTH: 21
<212> TYPE: DNA
<213> ORGANISM: Artificial Sequence
<220> FEATURE:
<223> OTHER INFORMATION: Chemically synthesized
<220> FEATURE:
<221> NAME/KEY: Primer
<222> LOCATION: (1)..(21)

<400> SEQUENCE: 1
ttactgaaca taaatcacag g                                              21

<210> SEQ ID NO 2
<211> LENGTH: 30
<212> TYPE: DNA
<213> ORGANISM: Artificial Sequence
<220> FEATURE:
<223> OTHER INFORMATION: Chemically synthesized
<220> FEATURE:
<221> NAME/KEY: Primer
<222> LOCATION: (1)..(30)

<400> SEQUENCE: 2
attattggta aatccttgct gcttattctc                                     30

<210> SEQ ID NO 3
<211> LENGTH: 23
<212> TYPE: DNA
<213> ORGANISM: Artificial Sequence
<220> FEATURE:
```

```
<223> OTHER INFORMATION: Chemically Synthesized
<220> FEATURE:
<221> NAME/KEY: Primer
<222> LOCATION: (1)..(23)

<400> SEQUENCE: 3
cagatgagcg gttcccttta tgc                                        23

<210> SEQ ID NO 4
<211> LENGTH: 28
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(28)

<400> SEQUENCE: 4
cagaagccat atcacctaat gtcatacc                                   28

<210> SEQ ID NO 5
<211> LENGTH: 30
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(30)

<400> SEQUENCE: 5
cgaatgggtt ggtagttctg gataataatc                                 30

<210> SEQ ID NO 6
<211> LENGTH: 32
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(32)

<400> SEQUENCE: 6
atgtgtatgt aggaattgac tttgaattta gc                              32

<210> SEQ ID NO 7
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 7
ctgctgggat agagtggctt aatac                                      25

<210> SEQ ID NO 8
<211> LENGTH: 25
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(25)

<400> SEQUENCE: 8
```
ctgctgggat agagtggctt aatac                                        25

<210> SEQ ID NO 9
<211> LENGTH: 22
<212> TYPE: DNA
<213> ORGANISM: Artificial Sequence
<220> FEATURE:
<223> OTHER INFORMATION: Chemcially Synthesized
<220> FEATURE:
<221> NAME/KEY: Primer
<222> LOCATION: (1)..(22)

<400> SEQUENCE: 9
gtgtttggtc gcatatcgca ac                                           22

<210> SEQ ID NO 10
<211> LENGTH: 26
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(26)

<400> SEQUENCE: 10
gctgtatcaa tcaaaagcaa ctcatc                                       26

<210> SEQ ID NO 11
<211> LENGTH: 23
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(23)

<400> SEQUENCE: 11
cctacaatct aacggcgacc aag                                          23

<210> SEQ ID NO 12
<211> LENGTH: 23
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(23)

<400> SEQUENCE: 12
aacggcgaag agacaatgac aac                                          23

<210> SEQ ID NO 13
<211> LENGTH: 23
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(23)

<400> SEQUENCE: 13
acacctggcg acctcagaga tac                                          23

<210> SEQ ID NO 14

```
-continued

<211> LENGTH: 26
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(26)

<400> SEQUENCE: 14
acttgaccga cagaggcaac taattc                                          26

<210> SEQ ID NO 15
<211> LENGTH: 23
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(23)

<400> SEQUENCE: 15
cagcggcagc agtttgttga ttg                                             23

<210> SEQ ID NO 16
<211> LENGTH: 23
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(23)

<400> SEQUENCE: 16
ccagacgacg gcatagtcat ttg                                             23

<210> SEQ ID NO 17
<211> LENGTH: 24
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(24)

<400> SEQUENCE: 17
aaacaaggga atgggtggag actg                                            24

<210> SEQ ID NO 18
<211> LENGTH: 27
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(27)

<400> SEQUENCE: 18
aaggtatgct ttgaatttgc gttgaac                                         27

<210> SEQ ID NO 19
<211> LENGTH: 29
<212> TYPE: DNA
<213> ORGANISM: Artificial Sequence
<220> FEATURE:
```

```
<223> OTHER INFORMATION: Chemically Synthesized
<220> FEATURE:
<221> NAME/KEY: Primer
<222> LOCATION: (1)..(29)

<400> SEQUENCE: 19
aataatgacg cctatctaat tgacactcc                                       29

<210> SEQ ID NO 20
<211> LENGTH: 23
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(23)

<400> SEQUENCE: 20
attccacccg tactgtcgct atg                                             23

<210> SEQ ID NO 21
<211> LENGTH: 24
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(24)

<400> SEQUENCE: 21
tgacgcctat ctgattgaca ctcc                                            24

<210> SEQ ID NO 22
<211> LENGTH: 23
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(23)

<400> SEQUENCE: 22
gctgtcgcta tggaaatgtg agg                                             23

<210> SEQ ID NO 23
<211> LENGTH: 28
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(28)

<400> SEQUENCE: 23
ccagtacaag aagttaattt tgccgatg                                        28

<210> SEQ ID NO 24
<211> LENGTH: 23
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(23)
```

```
<400> SEQUENCE: 24
cccaaccagt caaccaacct acc                                              23

<210> SEQ ID NO 25
<211> LENGTH: 29
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(29)

<400> SEQUENCE: 25
atattttact tgctatgtgg ttgcttctc                                        29

<210> SEQ ID NO 26
<211> LENGTH: 23
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(23)

<400> SEQUENCE: 26
tctccaatcc gatcagggca ttc                                              23

<210> SEQ ID NO 27
<211> LENGTH: 21
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(21)

<400> SEQUENCE: 27
agtgcccttc tcctgctttc c                                                21

<210> SEQ ID NO 28
<211> LENGTH: 20
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(20)

<400> SEQUENCE: 28
cctcgtcggc ggatctaacc                                                  20

<210> SEQ ID NO 29
<211> LENGTH: 28
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(28)

<400> SEQUENCE: 29
aatttattta acgaagcaca cactacgg                                         28
```

<210> SEQ ID NO 30
<211> LENGTH: 25
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(25)

<400> SEQUENCE: 30
gcacgagcaa gatcattacc atagc                                          25

<210> SEQ ID NO 31
<211> LENGTH: 18
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(18)

<400> SEQUENCE: 31
tgtgctgtgt tatctgac                                                  18

<210> SEQ ID NO 32
<211> LENGTH: 20
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(20)

<400> SEQUENCE: 32
gtgtttctgg acttctttac                                                20

<210> SEQ ID NO 33
<211> LENGTH: 23
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(23)

<400> SEQUENCE: 33
gacaattaca cctatacaag aag                                            23

<210> SEQ ID NO 34
<211> LENGTH: 20
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(20)

<400> SEQUENCE: 34
cgctctacat acaacatctc                                                20

<210> SEQ ID NO 35
<211> LENGTH: 18

```
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(18)

<400> SEQUENCE: 35
ttcgacgttc aagattcc                                                    18

<210> SEQ ID NO 36
<211> LENGTH: 18
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(18)

<400> SEQUENCE: 36
ttcgaaagcg gaaatctc                                                    18

<210> SEQ ID NO 37
<211> LENGTH: 21
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(21)

<400> SEQUENCE: 37
tgtcatgcct gccctgctat c                                                21

<210> SEQ ID NO 38
<211> LENGTH: 20
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(20)

<400> SEQUENCE: 38
acgaagtcca cctgctcacg                                                  20

<210> SEQ ID NO 39
<211> LENGTH: 18
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(18)

<400> SEQUENCE: 39
caggtgctct tcaacaag                                                    18

<210> SEQ ID NO 40
<211> LENGTH: 18
<212> TYPE: DNA
<213> ORGANISM: Artificial Sequence
<220> FEATURE:
<223> OTHER INFORMATION: Chemically Synthesized
```

```
<220> FEATURE:
<221> NAME/KEY: Primer
<222> LOCATION: (1)..(18)

<400> SEQUENCE: 40
cgccctcttt ctttcaac                                                 18

<210> SEQ ID NO 41
<211> LENGTH: 20
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(20)

<400> SEQUENCE: 41
cctggtgatg atagagatac                                               20

<210> SEQ ID NO 42
<211> LENGTH: 18
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(18)

<400> SEQUENCE: 42
ataatcgttg gctgtacc                                                 18

<210> SEQ ID NO 43
<211> LENGTH: 18
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(18)

<400> SEQUENCE: 43
actttaggtg aggcaatg                                                 18

<210> SEQ ID NO 44
<211> LENGTH: 21
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(21)

<400> SEQUENCE: 44
taacttcttg tactggtgta a                                             21

<210> SEQ ID NO 45
<211> LENGTH: 21
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(21)
```

```
<400> SEQUENCE: 45
gtcatagtat tcgtcgttag a                                              21

<210> SEQ ID NO 46
<211> LENGTH: 23
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(23)

<400> SEQUENCE: 46
gtaagagtgc tttaatgttc ata                                            23

<210> SEQ ID NO 47
<211> LENGTH: 18
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(18)

<400> SEQUENCE: 47
cgatcaaacc gttggaag                                                  18

<210> SEQ ID NO 48
<211> LENGTH: 21
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(21)

<400> SEQUENCE: 48
aaggaaaact tgatggaatt g                                              21

<210> SEQ ID NO 49
<211> LENGTH: 27
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(27)

<400> SEQUENCE: 49
ttactgaaca taaatcacag ggcgtag                                        27
```